United States Patent [19]

McWilliams

[11] 4,447,666

[45] May 8, 1984

[54] PARA-SELECTIVE ALKYLATION CATALYSTS AND PROCESSES

[75] Inventor: John P. McWilliams, Woodbury, N.J.

[73] Assignee: Mobil Oil Corporation, New York, N.Y.

[21] Appl. No.: 454,763

[22] Filed: Dec. 30, 1982

[51] Int. Cl.$^3$ .............................................. C07C 3/52
[52] U.S. Cl. .................................... 585/467; 585/468; 585/446; 502/261
[58] Field of Search ............................. 585/466, 467; 252/455 Z, 449

[56] References Cited

U.S. PATENT DOCUMENTS

| | | | |
|---|---|---|---|
| 4,034,053 | 7/1977 | Kaeding et al. | 585/467 |
| 4,158,024 | 6/1979 | Kaeding et al. | 585/467 |
| 4,377,718 | 3/1983 | Sato et al. | 585/467 |

*Primary Examiner*—Delbert E. Gantz
*Assistant Examiner*—A. Pal
*Attorney, Agent, or Firm*—A. J. McKillop; M. G. Gilman; E. F. Kenehan, Jr.

[57] ABSTRACT

A method is provided for preparing a para-selective, zeolite-based aromatics alkylation catalyst by treating a ZSM-5 type zeolite base catalyst composite with an aqueous magnesium nitrate solution and thereafter calcining the composite so treated. Such catalysts can be used in alkylation processes to provide alkylated aromatic product mixtures having exceptionally high concentrations of the para-dialkylbenzene isomer.

16 Claims, No Drawings

PARA-SELECTIVE ALKYLATION CATALYSTS AND PROCESSES

BACKGROUND OF THE INVENTION

1. Field of the Invention

This invention relates to preparation of improved zeolite-based catalysts especially useful for promoting the alkylation of mono-alkyl aromatic compounds to form a dialkyl substituted aromatic product enriched in the para (i.e., 1,4-)dialkyl benzene isomer. The invention also relates to a process for the alkylation, e.g., ethylation, of monoalkyl aromatic compounds, e.g. toluene or ethylbenzene, in a manner so as to maximize the production of the product para-isomer, to minimize the production of the product meta isomer and to substantially eliminate the production of the product ortho isomer.

2. Description of the Prior Art

Zeolite-containing compositions are well known catalysts for promoting conversion of aromatic hydrocarbons to dialkyl substituted aromatic compounds via alkylation, transalkylation, disproportionation and isomerization reactions. Numerous techniques are also known for modifying zeolite-based aromatics conversion catalysts of this type in order to provide catalysts which promote production of a reaction product which is enriched in the para-isomer of the desired disubstituted aromatic material. For example, Kaeding, U.S. Pat. No. 4,117,024, Issued Sept. 26, 1978 and assigned to Mobil Oil Corporation, the assignee of the instant invention, discloses a process for the conversion of toluene and/or ethyl benzene to its corresponding para ethyl alkylation product by carrying out the alkylation in the presence of hydrogen and using as a catalyst a crystalline aluminosilicate zeolite of specified acidity, sorption characteristics and Constraint Index. U.S. Pat. No. 4,117,024 discloses many materials which exemplify this genus of catalysts including, but not limited to, ZSM-5, ZSM-11, ZSM-12, ZSM-35, and ZSM-38. The patent also discloses that the zeolite material may be modified in one or more ways to improve the para-selectivity properties of the catalyst. This U.S. Pat. No. 4,117,024 is incorporated herein in its entirety by reference as setting forth applicable prior art relative to this invention.

Additionally, reference is further made to Kaeding and Young, U.S. Pat. No. 4,034,053, Issued July 5, 1977; Kaeding, U.S. Pat. No. 4,049,573, Issued Sept. 20, 1977; and Kaeding and Young, U.S. Pat. No. 4,086,287, Issued Apr. 25, 1978. All of these patents are also incorporated herein by reference in their entirety as setting forth additional applicable prior art involving the modification of zeolite based catalysts of this same general type in order to improve the para-selectivity characteristics thereof when such materials are used to promote various aromatic hydrocarbon conversion reactions, including alkylation of monoalkyl substituted aromatics to produce dialkylbenzene compounds.

Considering all of such prior art references together, a process has been designed for the commercial production of para-ethyltoluene by the catalytic ethylation of toluene with ethylene using cofed hydrogen. Such a process utilizes what was heretofore believed to be the best catalyst for maximizing para-isomer, minimizing meta-isomer, eliminating ortho isomer, providing high conversion of reactants to products and permitting low catalyst aging rate. This optimized prior art catalyst is a crystalline siliceous material of ZSM-5 topology, as characterized by significant x-ray diffraction pattern lines, which is composited with a binder and is then impregnated with both phosphorus and magnesium. This selected catalyst is made by a series of process steps comprising: preparing the siliceous crystalline zeolite; binding the zeolite with a matrix material, suitably alumina; steaming the resulting zeolite-containing composite; impregnating the composite with diammonium phosphate followed by filtering, drying and calcining the resulting phosphorus-impregnated composite; contacting the P-containing composite in a first magnesium impregnation stage with a magnesium acetate solution, followed by calcination; thereafter contacting the composite, in a second separate magnesium impregnation stage, with another batch of magnesium acetate solution, followed again by calcination to prepare the final from catalyst. The modified zeolite catalyst produced in this manner is well suited to use in the toluene ethylation process. As can be seen from the data presented in the referenced U.S. Pat. No. 4,117,024, an ethyl toluene product is thus produced having desirable isomeric distribution characteristics, with very advantageous catalyst life and conversion capability.

From the foregoing preparation description and referenced data, it can be seen that the prior art catalyst selected as the best for commercialization, i.e. a magnesium and phosphorus impregnated, alumina-bound zeolite material, achieves its best selectivity for ethylene alkylation of toluene to para-ethyltoluene at impregnant loadings of 7 and 3 weight percent respectively for magnesium and phosphorus, provided the catalyst composite into which these materials are impregnated is presteamed. Without wishing to be bound by theory, it is believed that the magnesium being impregnated onto such a catalyst can have a significant affinity for the binder portion of the catalyst composite. It is further believed that the initial treatment of the prior art catalyst composite with the phosphorus impregnant serves to "passivate" the binder material, thereby promoting greater association of magnesium with the zeolite portion of the composite upon subsequent treatment of the composite with the magnesium acetate solution. Since it is expected that it is magnesium associated with the zeolite material in such composite which provides the excellent selectivity characteristics of such prior art composites for production of para-ethyltoluene, the phosphorus followed by magnesium treatment of such composites serves to provide highly desirable toluene alkylation catalysts.

Notwithstanding the suitability of such prior art Mg-P-ZSM-5 type zeolite catalyst composites for use in the commercial-scale production of para-ethyltoluene, there are still several disadvantages associated with the large scale preparation of catalysts of this type in the manner described. For example, if the impregnated catalyst is not presteamed, para-ethyltoluene selectivity may not be as high as needed for some commercial production operations. Furthermore, magnesium impregnation concentration to the optimum 7 weight percent cannot generally be achieved during commercial scale catalyst production, when using a magnesium acetate impregnant solution, in a single impregnation. Multiple impregnations, with intermediate calcination, are usually required during commercial scale production to achieve the requisite 7% concentration of magnesium. Still further, even to achieve this result using multiple impregnations, it is necessary to use very concentrated aqueous magnesium acetate solutions, e.g. about 50 to 60 weight percent in water. Such solutions are very viscous and thus have to be utilized as impregnants at elevated temperatures, e.g. about 150° F., in order to reduce impregnant viscosity to acceptable impregnation levels.

All of the foregoing recited disadvantages of the previously selected optimum magnesium/phosphorus based alkylation catalyst composites should not be taken to in any way mean that such a catalyst was or is unsatisfactory. Quite to the contrary, such a prior catalyst is excellent, far superior to it predecessors and is quite well suited to use in the aromatics alkylation processes described. It is furthermore commercially manufacturable, albeit with some difficulty and expense. Notwithstanding the suitability of such prior art alkylation catalysts, there is nevertheless a continuing need to develop additional catalysts, catalyst preparation procedures and alkylation processes employing such catalysts which provide one or more performance or commercial advantages over similar catalysts, procedures and processes of the prior art.

Accordingly, it is an object of the present invention to provide an additional type of zeolite-based catalyst composite suitable for promoting the para-selective conversion of monoalkyl aromatics such as toluene to dialkylbenzene materials such as para-ethyltoluene. It is a further object of the present invention to provide such an additional type of alkylation catalyst which is substantially phosphorus-free but which nevertheless exhibits selectivity and activity characteristics comparable or superior to those of the hereinbefore described magnesium phosphorus alkylation catalysts of the prior art. It is further an object of the present invention to provide such an additional type of alkylation catalyst which, in comparison with preferred prior art catalysts is simpler and easier to manufacture via a novel method for catalyst preparation. It is a further object of the present invention to provide an aromatics alkylation process employing such an improved zeolite-based alkylation catalyst.

SUMMARY OF THE INVENTION

The present invention relates primarily to a method for preparing a novel improved phosphorus-free aromatics alkylation catalyst. This catalyst preparation method involves the essential steps of preparing a zeolite-containing base catalyst composite, contacting this base catalyst composite, preferably in a single stage operation, with an aqueous solution of a single selected impregnating compound, magnesium nitrate, and thereafter calcining the magnesium nitrate treated catalyst composite to form the desired aromatics alkylation catalyst.

The zeolite material used to form the base catalyst composite is a siliceous crystalline zeolite having a silica to alumina molar ratio of at least about 12, a Constraint Index within the approximate range of 1 to 12 and a zeolite crystal having a major dimension of from about 1 to 10 microns and a minor dimension of from about 0.2 to 4 microns. Such materials are exemplified by the zeolites ZSM-5, ZSM-11, ZSM-12, ZSM-23, ZSM-35, ZSM-38, and ZSM-48. The zeolite material is combined with an inorganic oxide binder or matrix material to form a catalyst composite comprising from about 1 to 99% by weight of the zeolite and from about 1 to 99% by weight of the binder.

The magnesium nitrate impregnation step is conducted under conditions and for a length of time suitable to incorporate from about 25% to 50% by weight of magnesium nitrate on to the base catalyst composite on an anhydrous basis. Since magnesium nitrate is the only catalyst modifier utilized, there need be no contact of the catalyst composite with any solutions of phosphorus compounds, and the resulting catalyst is therefore substantially phosphorus free.

The calcination step which renders the catalyst ready for use is carried out in a nitrogen or oxygen-containing atmosphere at a temperature of from about 200° C. to 565° C. Such calcination is conducted for a time sufficient to provide a ready-to-use alkylation catalyst that contains from about 4% to 8% by weight of magensium which is present in the catalyst at least in part as magnesium oxide.

The resulting magnesium impregnated, substantially phosphorus free zeolite composite can be suitably employed to promote alkylation (e.g., ethylation) of monoalkyl aromatics such as toluene to produce a dialkylbenzene product mixture enriched in the para-dialkylisomer, e.g. ethyltoluene mixtures enriched in para-ethyltoluene.

DETAILED DESCRIPTION OF THE INVENTION

In accordance with the present invention, base catalyst composites comprising a particular type of zeolite material are modified to provide catalysts which are especially useful for promoting para-selective alkylation of monoalkyl benzene compounds. The siliceous crystalline zeolites used in such base catalyst composites are members of a special class of zeolites that exhibits unusual properties. Although such zeolites have usually low alumina contents, i.e. high silica to alumina mole ratios, they are very active even when the silica to alumina mole ratio exceeds 30. Such activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type siliceous crystalline zeolites useful in this invention possess, in combination: a silica to alumina mole ratio of at least about 12; and a structure providing constrained access to the intracrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 and preferably at least 30 are useful in the base catalyst composites of the present invention, it is also preferred in some instances to use zeolites having substantially higher silica/alumina ratios, e.g., 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Thus, also to be included within the zeolite definition are substantially pure silica forms of the useful zeolites described herein, that is to say those zeolites having no measurable amount of aluminum (silica to alumina mole ratio of infinity) but which otherwise embody the characteristics disclosed.

Members of this particular class of zeolites, after activation, acquire an intracrystalline sorption capacity for normal hexane which is greater than that for water, i.e. they exhibit "hydrophobic" properties. The zeolites useful in the catalyst composites of this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

| Zeolite | C.I. |
|---|---|
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than a exclusive value. That is, a crystalline zeolite when identified by any combination of conditions within the testing definition set forth herein as having a Constraint Index in the range of 1 to 12 is intended to be included in the instant zeolite definition whether or not the same identical zeolite, when tested under other of the defined conditions, may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. No. 3,702,886 and U.S. Reissue Pat. No. Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference. ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is more particularly described in allowed U.S. patent application Ser. No. 343,131, filed Jan. 27, 1982, the content of which is incorporated herein by reference.

It is to be understood that by incorporating by reference the foregoing patents to describe examples of specific members of the zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific siliceous crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, alumina extraction and calcination, alone or in combinations. Natural minerals which may be so treated include ferrierite, brewsterite, stilbite, dachiardite, epistilbite, heulandite, and clinoptilolite.

The preferred siliceous crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired.

Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since memory will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| Z5M-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |

| | Void Volume | Framework Density |
|---|---|---|
| A | .5 | 1.3 |
| Y | .48 | 1.27 |

The size of the zeolite crystals employed in the alkylation catalyst composites of this invention can also affect the selective catalytic properties of such a catalyst. For highest selectivity to para-isomer alkylation, it is preferred that the size of the zeolite crystals utilized range from about 1 to 10 microns, more preferably from about 2 to 4 microns along the major dimension (crystal length) and from about 0.2 to 4 microns, more preferably from about 0.5 to 2 microns along the minor dimension (crystal thickness).

When synthesized in the alkali metal form, the zeolite used to form the base catalyst composite can be conveniently converted in a conventional manner to the hydrogen form, generally by intermediate formation of the ammonium form as a result of ammonium ion exchange and calcination of the ammonium form to yield the hydrogen form of the zeolite. In addition to the hydrogen form, other forms of the zeolite can be employed in the base catalyst composition so long as the original alkali metal has been reduced to less than about 50% by weight of the original alkali metal contained in the zeolite as-synthesized, usually 0.5% by weight or less. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In preparing the zeolite-containing base catalyst composites of the present invention, the above-described siliceous crystalline zeolite material is combined with a matrix comprising another material resistant to the temperature and other conditions employed in the process for preparing the modified catalyst composites of the present invention and/or in the subsequent aromatics alkylation process embodiments in which such catalyst composites are employed. Such matrix material is useful as a binder and imparts greater resistance to the catalyst for the severe temperature, pressure and reactant feed stream velocity conditions encountered in such processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the binder for the siliceous crystalline zeolite material employed herein can comprise a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 25 to about 80 percent by weight of the dry base composite.

In prior art processes for modifying base catalyst composites of the type hereinbefore described, such base catalyst composites of this type are frequently subjected at this point in catalyst preparation to a pre-steaming procedure as one step in the process of preparing para-selective aromatics alkylation catalysts. Such pre-steaming treatment serves to enhance the para-selectivity characteristics of the alkylation catalyst eventually prepared. It has been discovered that by employing the particular base catalyst composite treatment procedure hereinafter described, such a pre-steaming step can be eliminated and yet the para-selectivity of the resulting alkylation catalyst will be as good as or better than that of a steam selectivated Mg-P impregnated catalyst of the prior art.

Thus, as a second step in the catalyst preparation process of the present invention, the base catalyst composites prepared as hereinbefore described can be contacted with an aqueous solution of the particular selected catalyst modifying agent magnesium nitrate. Such contact of base catalyst composites with magnesium nitrate solution generally occurs under treatment conditions which are, and for a time period which is, sufficient to incorporate from about 25% to 50%, more preferably from about 30% to 43%, by weight of magnesium nitrate onto the base catalyst composite on an anhydrous basis.

The aqueous solution of magnesium nitrate used in this contacting step can be prepared by simply dissolving an appropriate form of magnesium nitrate, e.g., $Mg(NO_3)_2 \cdot 2H_2O$ or $Mg(NO_3)_2 \cdot 6H_2O$, with water to form the treating solution for the base catalyst composites. If desired, inert cosolvents such as lower alkanols can be employed in forming this magnesium nitrate solution. Magnesium nitrate concentrations of from about 40% to 65%, more preferably from about 60% to 65%, by weight of solution can advantageously be employed in forming the magnesium nitrate composite treating solution.

Contact between base catalyst composites and magnesium nitrate solution can be effected by any suitable means conventionally used to treat solid particulate material with a treating agent in liquid form. Such techniques can, for example, involve soaking the base catalyst composites in the magnesium nitrate solution in a suitable vessel or may involve continuous or intermittent contact of the magnesium nitrate solution with a bed of catalyst composite particles. The ebullated bed arrangement of Bowes; U.S. Pat. No. 4,292,205; issued Sept. 29, 1981, incorporated herein by reference, represents another useful means for effecting catalyst contact with the magnesium nitrate treating solution.

No matter what particular contact arrangement may be employed, the handling of the magnesium nitrate solution in such procedures is generally much easier than the handling of the impregnating solutions in corresponding prior art procedures which utilize comparatively much more viscous solutions of magnesium acetate. The viscous behavior of concentrated magnesium acetate solutions can make catalyst impregnation difficult in such prior art processes since channeling and catalyst flotation may become problems in larger vessels used for impregnation. Catalyst treatment using magnesium nitrate solutions, on the other hand, can be accomplished with fewer processing and equipment difficulties in comparison with magnesium acetate impregnation. It is furthermore apparent that since the magnesium nitrate treated catalyst composites are not to be phosphorus-modified, the composites of the present invention are not therefore contacted with solutions of phosphorus compounds either prior to or subsequent to their treatment with the magnesium nitrate solution.

The efficiency of commercial scale catalyst composite impregnation is also significantly improved with magnesium nitrate impregnation in comparison with impregnation using aqueous magnesium acetate solution. Using magnesium nitrate solutions, it is in fact possible to incorporate the requisite amount of magnesium onto the catalyst composite in a single impregnation stage without intermediate drying or calcination, provided the impregnated catalyst material is dried by free convection methods. Even when forced convection gas is used to dry the impregnated composites (thereby blowing some of the impregnating solution off the catalyst material), it is possible to reach optimum magnesium content using a magnesium nitrate impregnant in as few as two impregnation stages.

As noted, contact between magnesium nitrate treating solution and the base catalyst composites occurs for a time period which is sufficient to effect incorporation of the requisite amount of magnesium nitrate onto the base catalyst composites. Contact times of at least about 0.5 hour, more preferably from about 1 to 2 hours, may advantageously be utilized. Contacting conditions will generally also include a contact temperature from about 10° C. to 65° C., more preferably from about 20° C. to 55° C. The resulting impregnated composites will generally contain from about 25% to 50% by weight, more preferably from about 30% to 45% by weight, of magnesium nitrate on an anhydrous basis.

After contact of the catalyst composites with magnesium nitrate solution is completed to the extent desired, the treated catalyst composites can thereafter be dried and calcined to form the finished catalyst compositions suitable for use in promoting para-selective alkylation reactions. Calcination will generally occur in a nitrogen and/or oxygen-containing atmosphere, e.g. air, which may also contain diluents such as helium and the like. Calcination can be carried out at a temperature of from about 200° C. to 565° C., more preferably from about 510° C. to 540° C., and for a time sufficient to provide a modified catalyst composition containing from about 4% to 8%, more preferably from about 6% to 7%, by weight of magnesium on the finished catalyst composition. At least some of the magnesium present in the calcined catalyst composition is thus present in the form of magnesium oxide. Calcination under such conditions can thus advantageously be carried out for a period of from about 1 to 6 hours, more preferably from about 2 to 6 hours.

The magnesium nitrate treated zeolite catalysts of the present invention can be advantageously used to promote conversion of mono-alkyl aromatic compounds to provide dialkyl substituted benzene product mixtures which are highly enriched in the para-dialkyl substituted benzene isomer. Conversion reactions of this type thus involve an aromatics alkylation reaction. Alkylation of aromatic compounds in the presence of the above-described catalysts can be effected by contact of the aromatic with an alkylating agent under alkylatio conditions. A particularly preferred embodiment involves the alkylation of toluene wherein the alkylating agents employed comprise methanol or other well known methylating agents or ethylene. The reaction is carried out at a temperature of between about 250° C. and about 750° C., preferably between about 300° C. and 650° C. At higher temperatures, the zeolites of high silica/alumina ratio are preferred. For example, ZSM-5 having a $SiO_2/Al_2O_3$ ratio of 30 and upwards is exceptionally stable at high temperatures. The reaction generally takes place at atmospheric pressure, but pressures within the approximate range of $10^5$ n/m$^2$ to $10^7$ N/m$^2$ (1–100 atmospheres) may be employed.

Some non-limiting examples of suitable alkylating agents would include olefins such as, for example, ethylene, propylene, butene, decene and dodecene, as well as formaldehyde, alkyl halides and alcohols, the alkyl portion thereof having from 1 to 16 carbon atoms. Numerous other aliphatic compounds having at least one reactive alkyl radical may be utilized as alkylating agents.

Aromatic compounds which may be selectively alkylated as described herein would include any alkylatable mono-alkyl aromatic hydrocarbon such as, for example, ethylbenzene, toluene, propylbenzene, ispropylbenzene, or substantially any mono-substituted benzenes which are alkylatable in the 4-position of the aromatic ring.

The molar ratio of alkylating agent to aromatic compound is generally between about 0.05 and about 2. For instance, when methanol is employed as the methylating agent and toluene is the aromatic, a suitable molar ratio of methanol to toluene has been found to be approximately 0.1 to 1.0 mole of methanol per mole of toluene. When ethylene is employed a the alkylating agent and toluene is the aromatic, a suitable molar ratio of ethylene to toluene is approximately 0.05 to 2.5 moles of ethylene per mole of toluene.

Alkylation is suitably accomplished utilizing a feed weight hourly space velocity (WHSV) of between about 1 and about 100, and preferably between about 1 and about 50. The reaction product, consisting predominantly of the 1,4-dialkyl isomer, e.g. 1,4-dimethylbenzene, 1-ethyl-4-methylbenzene, etc., or a mixture of the 1,4- and 1,3-isomer, may be separted by any suitable means. Such means may include, for example, passing the reaction product stream through a water condenser and subsequently passing the organic phase through a column in which chromatographic separation of the aromatic isomers is accomplished. Alkylation using the magnesium nitrate-treated catalysts of the present invention can provide product mixtures containing at least 80% or even 90% or more by weight of the para-dialkylbenzene isomer.

The aromatics alkylation process described herein may be carried out as batch type, semi-continuous or continuous operations utilizing a fluid or moving bed catalyst system. The catalyst after use in a moving bed reactor can be conducted to a regeneration zone wherein coke is burned from the catalyst in an oxygen-containing atmosphere, e.g. air, at an elevated temperature, after which the regenerated catalyst can be recycled to the alkylation zone for further contact with the charge stock. In a fixed bed reactor, regeneration can be carried out in a conventional manner where an inert gas containing a small aount of oxygen (0.5–2%) is used to burn the coke in a controlled manner so as to limit the temperature to a maximum of around 500° C.-550° C.

Siliceous zeolite crystal-containing composites treated with magnesium nitrate according to this invention show remarkably better catalytic properties for the alkylation of monoalkylbenzene than do corresponding composites impregnated with magnesium acetate to the same magnesium content. It is recognized that the above referenced U.S. Pat. No. 4,117,024 describes and claims siliceous crystals impregnated with one or more of phosphorus, boron, antimony or magnesium and that this patent describes a host of magnesium introducing impregnants including inter alia magnesium acetate and magnesium nitrate (see Column 10, line 15 et seq.). It is also recognized that U.S. Pat. No. 4,117,024 describes and prefers the use of relatively large crystals, about 1 to 5 microns, (see Column 12, lines 51 et seq.) of siliceous zeolite materials. However U.S. Pat. No. 4,117,024 does not recognize that crystal-containing composites impregnated with magnesium nitrate are not equivalent to such composite impregnated with other magnesium salts, notably magnesium acetate, for the alkylation, e.g., ethylation, of mono substituted, particularly alkylated, most particularly methyl, benzenes to produce the desired product distribution described above in an optimal fashion. The particular magnesium-containing composites of the present invention which have been prepared using a magnesium nitrate impregnant in fact represent catalysts which provide improved conversion of monoalkylaromatics ot dialkylaromatics, with improved selectivity of such conversion to production of para-dialkyl aromatic isomers and with reduced time off-stream for catalyst regeneration and re-selectivation.

Without being bound to any particular theory of invention operability, it is speculated that the catalyst performance benefits achieved with the magnesium nitrate impregnated catalyst composite result from the enhanced tendency of magnesium nitrate solutions to deliver magnesium to the siliceous zeolite crystal portion of the catalyst composite versus the binder portion of the composite. It is perhaps this enhanced incorporation of magnesium from $MgNO_3$ into the siliceous zeolite crystalline material which permits elimination of the binder passivating phosphorus treatment step which is necessary to produce composites of desirably high para-selectivity when a magnesium acetate impregnant is employed.

The following examples will serve to illustrate certain specific embodiments of the hereindisclosed invention. These examples should not, however, be construed as limiting the scope of the invention, as there are many variations which may be made thereon without departing from the spirit of the disclosed invention, as those of skill in the art will recognize.

EXAMPLE I

Part A—Converting Extrudate to Ammonium Form

Untreated base catalyst composites utilized are in the form of 1/6" extrudate containing 65% by weight ZSM-5 and 35% by weight alumina binder. ZSM-5 crystal size in such composites is approximately 1 micron in length, 0.5 micron in thickness. Six pounds (2728 g; 4200 cc) of this dried extrudate are charged to an ion exchange/calcination vessel. Extrudate therein is pre-calcined in $N_2$ at 540° C. for 3 hours at a flow rate of 1.25 SCFM.

After cooling, the extrudate is ion exchanged with 42 pounds of 1 N ammonium nitrate solution at room temperature for one hour. After draining, the procedure is repeated and followed by 5 volumetric washes with deionized water. (Each is one complete fill followed by draining.)

The extrudate is then dried in warm flowing $N_2$ and sampled. Sodium content is less than 0.01 wt. %. The zeolitic portion of the extrudate is now in the ammonium form with the extrudate having the following composition:

65% $NH_4$—ZSM-5
35% Alumina

Part B—First Magnesium Impregnation

Twelve kilograms of 60% weight $Mg(NO_3)_2.6H_2O$ are prepared. This solution is introduced to the ammonium form extrudate still in place in the ion exchange/calcination vessel. The solution is pumped upflow in a recycle mode for 5 minutes, then allowed to stand for one hour, all at room temperature. Before draining, the solution is again circulated for 5 minutes at 650 cc/min. Solution is then drained and the extrudate dried in warm $N_2$ at a flow of 0.55 SCFM.

After all points in the bed registered greater than 250° F. (120° C.), the extrudate is considered completely dry. Gas flow rate is increased to 1.25 SCFM and temperatures increased to effect calcination. When bed temperatures are approximately 425° C. (800° F.), gas composition is changed to air, and the temperature increased to approximately 540° C. (1000° F.) and held for 2 hours. The bed is then cooled in $N_2$ and sampled.

The sample is found to have 3.8 wt. % Mg and an alpha activity of 51.

Part C—Second Magnesium Impregnation 7.9 Kg of magnesium nitrate solution recovered from the first impregnation is supplemented with 2.1 Kg of fresh 60% $Mg(NO_3)_2.6H_2O$ to effect a second impregnation of the extrudate still in the vessel. The procedure is exactly as described for the first impregnation, including draining, drying and calcination. After cooling, the contents of the vessel are discharged. The finished catalyst is characterized as follows:

Weight: 2347 g
Wt. % Mg: 6.6
% Ash (1000° C.): 96.78
Alpha Activity: 28

EXAMPLE II

A large scale batch of ammonium form extrudate is prepared as described in Part A of Example I. A sample of this extrudate (800 cc) is steamed in laboratory steamers (400 cc each) in 100% steam, at one atmosphere and 540° C. (1000° F.) for 5 hours.

A sample of the steamed extrudate (100 cc) is impregnated in a beaker with 200 cc of a 66 wt. % solution of $Mg(NO_3)_2.6H_2O$ for one hour at room temperature, with occasional stirring. The extrudate is drained on a screen, placed in a porcelain evaporating dish which is placed in a laboratory drier kept at 120° C. (250° F.), and allowed to dry over a weekend.

The dried impregnated extrudate is then placed in a one pint muffle pot (a device to hold catalyst and allow positive gas flow from outside a muffle furnace) and is heated in 300 cc/min of $N_2$ to a temperature of about 425° (800° F.). At this point $N_2$ is replaced by air and the temperature of the impregnated extrudate is increased to 540° C. (1000° F.) and held for two hours. The sample is cooled down in $N_2$.

Such a catalyst sample has a magnesium content of 7.0% by weight.

EXAMPLE III

The procedure of Example II is repeated with a separate sample of ammonium form ZSM-5 extrudate. In this procedure, however, the concentration of the impregnating solution is 60% by weight $Mg(NO_3)_2.6H_2O$.

Such a catalyst sample has a magnesium content of 6.4% by weight.

EXAMPLE IV

A 50 cc sample of the ammonium form ZSM-5 extrudate of Example I is calcined in $N_2$ for 3 hours at 540° C. (1000° F.). The cooled sample is then impregnated at 55° C. (130° F.) with 100 cc of a 60% $Mg(OAc)_2.4H_2O$ solution for 2 hours. The sample is drained, dried and calcined as described in Example II.

Such a catalyst sample has a magnesium content of 7.3% by weight.

EXAMPLE V

A 100 cc sample of the ammonium form ZSM-5 extrudate of Example I is calcined in $N_2$ for 3 hours at 540° C. (1000° F.). The sample is cooled and impregnated with 60% $Mg(NO_3)_2.6H_2O$ (200 cc) for one hour at room temperature. The sample is then drained, dried and calcined as described in Example II.

Such a catalyst sample has a magnesium content of 6.9% by weight.

EXAMPLE VI

A 100 cc sample of another batch of ammonium form ZSM-5 extrudate prepared in a manner substantially similar to that of Example I is impregnated with Mg using 200 cc of a 60% solution of $Mg(NO_3)_2.6H_2O$ for one hour at 55° C. (130° F.). The sample is then drained, dried and calcined as described in Example II.

Such a catalyst sample has a magnesium content of 6.8% by weight.

EXAMPLE VII

A 50 cc sample of the same batch of ammonium form ZSM-5 extrudate of Example VI is impregnated using 100 cc of 55% $Mg(NO_3)_2.6H_2O$ solution for one hour at room temperature (approximately 75° F.). The sample is then drained, dried and calcined as described in Example II.

Such a catalyst sample has a magnesium content of 6.2% by weight.

EXAMPLE VIII

The procedure of Example VII is repeated with a separate sample of the same ammonium form ZSM-5 extrudate. In this procedure, however, the concentration of the impregnating solution is 50% by weight of $Mg(NO_3)_2.6H_2O$.

Such a catalyst sample has a magnesium content of 5.4% by weight.

EXAMPLE IX

A 50 cc sample of the ammonium form ZSM-5 extrudate from the ion exchange/calcination vessel of Example I is impregnated with 100 cc of 60% $Mg(NO_3)_2.6H_2O$ for one hour at room temperature (approximately 75° F.).

Such a catalyst sample has a magnesium content of 7.3% by weight.

EXAMPLE X

Approximately 4,800 lbs. of untreated ZSM-5 base catalyst composites of the type described in Example I, Part A, are charged to an ion exchange/calcination vessel. The bed of extrudate in the vessel is heated in $N_2$ to 1000° F. and held for 3 hours (640 SCFM of $N_2$). After cooling in $N_2$, the bed is ion-exchanged with a solution made up from 600 lbs. of ammonium nitrate and 2,530 gallons of deionized water for 3 hours at ambient temperature with a circulation of 100 gallons per minute. After draining and washing with 2,500 gallons of deionized water, the procedure is repeated. A sample from the bed, after drying analyzes at 0.01 wt. % Na.

The bed is dried, unloaded and split in half. One half, i.e. 2,393 lbs., are reloaded into the vessel. The bed is impregnated with a 60% weight solution of $Mg(NO_3)_2.6H_2O$ made by dissolving 10,500 lbs. of $Mg(NO_3)_2.6H_2O$ in 839 gallons of deionized water. After the bed is completely wetted, solution is circulated for 15 minutes at 650 gallons per minute. Solution is allowed to stand for one hour and is then recirculated again for 15 minutes. Solution is then drained by pumping solution back to the original solution tank.

The treated extrudate is then dried by flow of air (130 SCFM) at 450° F. leaving the furnace. After 48 hours, the bed is considered completely dry (all temperatures above 325° F.), and flow is switched to $N_2$ and increased to 720 SCFM for calcination. The furnace temperature is increased, and at an average bed temperature of 800° F., the furnace is held constant for 2 hours. $N_2$ is then replaced with air, and the furnace temperature is increased to give a temperature of 1000° F. in the bed. These conditions are held for 2 hours. The bed is then cooled in air to 400° F., then in $N_2$ to less than 125° F. and sampled.

At this point a second batch of impregnated catalyst is made. The first batch of 2,400 lbs. is discharged from the ion exchange/calcination vessel. The remaining dried extrudate is loaded into the vessel, and the foregoing impregnation procedure is repeated exactly. The two batches are then combined in the vessel for one final impregnation.

The final impregnation step, draining, drying and calcination are exactly as hereinbefore described except that the vessel contains about 4,800 lbs. of extrudate. Magnesium nitrate solution is reused from the solution task. Intermediate samples and final products have the following characteristics.

|  | Alpha Activity | Wt. % Mg |
| --- | --- | --- |
| First Batch, First Impregnation | 32 | 3.4 |
| Second Batch, First Impregnation | 35 | — |
| Final Product | 27 | 7.0 |

EXAMPLE XI

The catalyst samples from the foregoing examples are tested for their ability to promote alkylation of toluene with ethylene. In the procedure for conducting such testing, approximately 15 cc of catalyst are charged to a ⅜" diameter stainless steel reactor fitted with a central thermowell. The reactor is placed in a three zone split furnace and heated in flowing $N_2$ to 800° F. $N_2$ is then replaced by $H_2$, toluene is introduced, followed by ethylene. The inlet temperature to the reactor is adjusted to 810° F. The pressure is controlled at 100 psig inlet to the reactor, and the flows are adjusted to give an 8.8:1:3 molar ratio of toluene/ethylene/hydrogen. On a WHSV basis, this is 29:1:0.2 (i.e. 29 g toluene/g catalyst/hour).

Two hours after introduction of ethylene (line-out period), collection of the liquid product is begun. After one hour, the product is removed, weighed and analyzed by gas chromatograph. Gas produced during the hour is also measured volumetrically and analyzed by mass spectroscopy.

Data from these analyses are combined by computer program to give an overall material-balanced run result. Especially noted is the proportion of para-ethyltoluene in ethyltoluenes, PET/ET, and the ratio of toluene converted to theoretical toluene conversion if all ethylene fed reacted stoichiometrically with toluene to give ethyltoluene.

Results for such testing of catalyst samples from Examples I–X are set forth in Table I.

TABLE I

Alkylation of Toluene with Ethylene Over Mg ZSM-5 Catalysts

| Catalyst Sample | Impregnant | % Wt. Mg | PET/ET % | Toluene Conversion % |
|---|---|---|---|---|
| Example I | $Mg(NO_3)_2.6H_2O$ | 6.6 | 99.2 | 86 |
| Example II | $Mg(NO_3)_2.6H_2O$ | 7.0 | 95 | 65 |
| Example III | $Mg(NO_3)_2.6H_2O$ | 6.4 | 93 | 78 |
| Example IV | $Mg(OAc)_2.4H_2O$ | 7.3 | 83 | 94 |
| Example V | $Mg(NO_3)_2.6H_2O$ | 6.9 | 97 | 88 |
| Example VI | $Mg(NO_3)_2.6H_2O$ | 6.8 | 94 | 88 |
| Example VII | $Mg(NO_3)_2.6H_2O$ | 6.2 | 84 | 92 |
| Example VIII | $Mg(NO_3)_2.6H_2O$ | 5.4 | 67 | 100 |
| Example IX | $Mg(NO_3)_2.6H_2O$ | 7.3 | 97 | 88 |
| Example X, First Batch | $Mg(NO_3)_2.6H_2O$ | 3.4 | 52.6 | 98 |
| Example X, Second Batch | $Mg(NO_3)_2.6H_2O$ | — | 51.2 | 99 |
| Example X, Final Product | $Mg(NO_3)_2.6H_2O$ | 7.0 | 97.6 | 89 |

What is claimed is:

1. A method for making an improved magnesium-containing, zeolite-based alkylation catalyst composition especially suitable for promoting the alkylation of mono-substituted aromatic compounds to produce a disubstituted aromatic product enriched in the 1,4-isomer of the resulting disubstituted aromatic compound, said method comprising:
   (a) preparing a base catalyst composite comprising from about 25% to 80% by weight of a siliceous crystalline zeolite material characterized by a silica to alumina mole ratio of at least about 12, a Constraint Index within the approximate range of from about 1 to 12, a zeolite crystal major dimension of from about 1 to 10 microns, and a zeolite crystal minor dimension of from about 0.2 to 4 microns; said composite further comprising from about 20% to 75% by weight of an inorganic oxide binder;
   (b) contacting said base catalyst composite with an aqueous solution of magnesium nitrate under contacting conditions, and for a period of time sufficient to incorporate magnesium nitrate onto said base catalyst composite; said contact of catalyst composite with said magnesium nitrate solution occurring without either prior or subsequent contact of said composite with solutions of phosphorus compounds; and
   (c) calcining said magnesium nitrate-treated catalyst composite in a nitrogen-containing or oxygen-containing atmosphere at a temperature of from about 200° C. to 565° C. for a period of time sufficient to form an aromatics alkylation catalyst composition which contains from about 4% to 8% by weight of magnesium present at least in part as magnesium oxide, said alkylation catalyst composition being substantially free of phosphorus.

2. A method according to claim 1 wherein said contacting of base catalyst composite occurs in a single stage operation without intermediate calcination of said composite.

3. A method according to claim 1 wherein said siliceous crystalline zeolite is selected from the group consisting of ZSM-5, ZSM-11, ZSM-12, ZSM-23, ZSM-35, ZSM-38 and ZSM-48.

4. A method according to claim 3 wherein said zeolite crystal major dimension ranges from about 2 to 4 microns and said zeolite crystal minor dimension ranges from about 0.5 to 2 microns.

5. A method according to claim 3 wherein said aqueous solution of magnesium nitrate used to contact said base catalyst composite comprises $Mg(NO_3)_2.6H_2O$ present to the extent of from about 40% to 65% by weight of solution.

6. A method according to claim 5 wherein contact of magnesium nitrate solution with base catalyst composite occurs for a period of at least about 0.5 hour at a temperature of from about 10° C. to 65° C.

7. A method according to claim 5 wherein said crystalline zeolite is ZSM-5.

8. A method according to claim 3 wherein calcination occurs at a temperature of from about 510° C. to 540° C. for a period of from about 1 to 6 hours.

9. A method according to claim 3 wherein:
   (a) the magnesium nitrate content of said magnesium nitrate solution ranges from about 60% to 65% by weight of solution;
   (b) the calcined aromatics alkylation catalyst composition comprises from about 6% to 7% by weight of magnesium.

10. A substantially phosphorus-free, magnesium-containing, zeolite-based, aromatics alkylation catalyst composition prepared in accordance with the method of claim 1.

11. A substantially phosphorus-free, magnesium-containing, zeolite-based, aromatics alkylation catalyst composition prepared in accordance with the method of claim 7.

12. A process for the alkylation of monoalkyl substituted compounds to produce a dialkyl-substituted benzene compound mixture enriched in the para-dialkylbenzene isomer, said process comprising contacting a monoalkyl substituted aromatic compound with an alkylating agent under aromatic alkylation conditions in the presence of a substantially phosphorus-free, magnesium-containing, zeolite-based alkylation catalyst composition made by
   (a) preparing a base catalyst composite comprising from about 25% to 80% by weight of a siliceous crystalline zeolite material characterized by a silica to alumina mole ratio of at least about 12, a Constraint Index within the approximate range of from about 1 to 12, a zeolite crystal major dimension of from about 1 to 10 microns, and a zeolite crystal minor dimension of from about 0.2 to 4 microns; said composite further comprising from about 20% to 75% by weight of an inorganic oxide binder;

(b) contacting said base catalyst composite with an aqueous solution of magnesium nitrate under contacting conditions, and for a period of time, sufficient to incorporate magnesium nitrate onto said base catalyst composite; said contact of catalyst composite with said magnesium nitrate solution occurring without either prior or subsequent contact of said composite with solutions of phosphorus compounds; and (c) calcining said magnesium nitrate-treated catalyst composite in a nitrogen-containing or oxygen-containing atmosphere at a temperature of from about 200° C. to 565° C. for a period of time sufficient to form said aromatics alkylation catalyst composition which contains from about 4% to 8% by weight of magnesium present at least in part as magnesium oxide.

13. An alkylation process according to claim 12 wherein said alkylation conditions include a reaction temperature of between about 300° C. and 650° C., a molar ratio of alkylating agent to aromatic compound of from about 0.05 to 2 and a weight hourly space velocity of reactant feed of from about 1 to 50.

14. An alkylation process according to claim 13 wherein said aromatic compound is selected from toluene and ethylbenzene and said alkylating agent contains from 1 to about 16 carbon atoms and is selected from olefins, alkyl halides and alkanols.

15. An alkylation process according to claim 14 wherein said aromatic compound is toluene and said alkylating agent is ethylene.

16. An alkylation process according to claim 15 wherein said siliceous crystalline zeolite material is ZSM-5.

* * * * *